(12) United States Patent
Wang (10) Patent No.: US 7,037,318 B2
(45) Date of Patent: May 2, 2006

(54) CATHETER FOR CONTROLLED STENT DELIVERY

(75) Inventor: Lixiao Wang, Long Lake, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 66 days.

(21) Appl. No.: 09/740,101

(22) Filed: Dec. 18, 2000

(65) Prior Publication Data

US 2002/0077690 A1    Jun. 20, 2002

(51) Int. Cl.
*A61M 29/00*    (2006.01)

(52) U.S. Cl. .................................... 606/191

(58) Field of Classification Search ............... 606/191, 606/194, 192, 108, 195, 159; 604/96, 103.07
See application file for complete search history.

(56) References Cited

U.S. PATENT DOCUMENTS

| | | | |
|---|---|---|---|
| 4,950,227 A | 8/1990 | Savin et al. ............... 604/8 |
| 5,084,060 A * | 1/1992 | Freund et al. ............. 606/192 |
| 5,108,416 A | 4/1992 | Ryan et al. ............... 606/194 |
| 5,316,016 A * | 5/1994 | Adams et al. ............ 128/774 |
| 5,338,298 A | 8/1994 | McIntyre ................. 604/96 |
| 5,352,199 A * | 10/1994 | Tower ..................... 604/96 |
| 5,403,341 A | 4/1995 | Solar ...................... 606/198 |
| 5,415,635 A * | 5/1995 | Bagaoisan et al. ........ 604/96 |
| 5,470,313 A * | 11/1995 | Crocker et al. ........... 604/96 |
| 5,556,383 A | 9/1996 | Wang et al. .............. 604/96 |
| 5,632,760 A | 5/1997 | Shieban et al. .......... 606/191 |
| 5,645,560 A | 7/1997 | Crocker et al. ........... 606/192 |
| 5,738,901 A | 4/1998 | Wang et al. .............. 427/2.3 |
| 5,749,851 A | 5/1998 | Wang ..................... 604/96 |
| 5,766,201 A | 6/1998 | Ravenscroft et al. ...... 606/194 |
| 5,836,965 A | 11/1998 | Jendersee et al. ........ 606/198 |
| 5,843,116 A | 12/1998 | Crocker et al. ........... 606/192 |
| 6,024,752 A | 2/2000 | Horn et al. ............... 606/192 |
| 6,027,517 A | 2/2000 | Crocker .................. 606/192 |
| 6,048,350 A | 4/2000 | Vrba ...................... 606/108 |
| 6,120,523 A | 9/2000 | Crocker et al. ........... 606/192 |

(Continued)

FOREIGN PATENT DOCUMENTS

EP    1 000 593 A2    5/2000

(Continued)

OTHER PUBLICATIONS

U.S. Appl. No. 08/685,338, filed Jul. 23, 1996, Wang.

(Continued)

*Primary Examiner*—Alissa L. Hoey
(74) *Attorney, Agent, or Firm*—Vidas, Arrett & Steinkraus (57) ABSTRACT

A catheter having a catheter shaft and a medical balloon mounted thereon. The medical balloon having a non-inflated state and being inflatable to an inflated state. The medical balloon having a stent mounting region, with a stent being disposed about at least a portion of the stent mounting region. The stent mounting region having a middle portion, a first end portion adjacent to the middle portion and a second end portion adjacent to the middle portion. The middle portion having a middle portion diameter, the first end portion having a first end portion diameter, the second end portion having a second end portion diameter. In the non-inflated state the middle portion diameter being different from the first end portion diameter and the second end portion diameter, in the inflated state the middle portion diameter being substantially the same as the first end portion diameter and the second end portion diameter.

16 Claims, 7 Drawing Sheets

U.S. PATENT DOCUMENTS

| | | | | |
|---|---|---|---|---|
| 6,126,634 | A | * | 10/2000 | Bagaoisan et al. ............ 604/96 |
| 6,129,737 | A | * | 10/2000 | Hamilton et al. ............ 606/194 |
| 6,221,043 | B1 | * | 4/2001 | Fischell et al. ......... 604/103.07 |
| 6,280,412 | B1 | * | 8/2001 | Pederson, Jr. et al. .. 604/103.07 |
| 6,293,959 | B1 | * | 9/2001 | Miller et al. ................. 606/194 |
| 6,383,212 | B1 | * | 5/2002 | Durcan et al. .............. 623/1.11 |
| 6,409,741 | B1 | | 6/2002 | Crocker et al. ............. 606/192 |
| 6,432,080 | B1 | * | 8/2002 | Pederson, Jr. et al. .. 604/103.07 |
| 2003/0028211 | A1 | | 2/2003 | Crocker et al. ............. 606/192 |

FOREIGN PATENT DOCUMENTS

WO          00/03662          1/2000

OTHER PUBLICATIONS

U.S. Appl. No. 09/335,561, filed Jun. 17, 1999, Seppela et al.

U.S. Appl. No. 09/407,836, filed Sep. 28, 1999, Wang et al.

U.S. Appl. No. 08/740,727, filed Nov. 1, 1996, Sydney et al.

\* cited by examiner

CATHETER FOR CONTROLLED STENT DELIVERY

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

This invention relates to a medical balloon for use in expanding or seating a medical device such as a stent at a desired bodily location. More specifically, this invention relates to a stent delivery system wherein the balloon in the unexpaned state has a central balloon section having a diameter which is different than the respective diameters of adjacent balloon sections. When the balloon is expanded the unique shape of the balloon provides an engagement surface which reduces longitudinal movement of an associated medical device such as a stent, stent-graft, graft or vena cava filter mounted thereon during balloon expansion. In addition, the shape of the balloon encourages stent retaining sleeves or socks to be readily retracted from the balloon. The diameter of the central or middle portion of the balloon may be greater than or less than the adjacent portions of the balloon in the non-inflated state.

2. Description of the Related Art

Expandable, implantable medical devices such as stents are utilized in a number of medical procedures and situations as are stent delivery assemblies. As such, their structure and function are well known. A stent is a generally cylindrical prosthesis introduced via a catheter into a lumen of a body vessel in a configuration having a generally reduced diameter and then expanded to the diameter of the vessel. The stent may be self-expanding, such as a NITINOL shape memory stent, or it may be expandable by means of an inflatable portion of the catheter, such as a balloon. In its expanded configuration, the stent supports and reinforces the vessel walls while maintaining the vessel in an open, unobstructed condition.

Self-expanding, inflation assisted expandable and inflation expandable stents are well known and widely available in a variety of designs and configurations. Inflation expandable and inflation assisted expandable stents are expanded via outward radial pressure such as that provided by a balloon disposed underneath the stent during inflation of the balloon.

Medical device delivery balloons may have a variety of shapes, sizes, inflation characteristics and a variety of other performance attributes. Some examples of balloons which may be used for the expansion and delivery of a medical device are described in U.S. Pat. Nos. 5,749,851; 5,556,383; 5,738,901; 6,024,752; and 6,048,350.

In advancing an inflation expandable stent through a body vessel to the deployment site, there are a number of important considerations. The stent must be able to securely maintain its axial position on the delivery catheter, without translocating proximally or distally, and especially without becoming separated from the catheter. Furthermore, it may be desirable to protect the distal and proximal ends of the stent to prevent distortion of the stent and to prevent abrasion and/or to reduce potential trauma to the vessel walls.

To address the concerns stated above, one approach has been identified which utilizes a retractable sheath or sheaths which are disposed about the distal end of the catheter and cover the stent and balloon. In such devices the sheath is retracted prior to the inflation of the balloon and subsequent delivery of the stent. Another solution involves the utilization of one or more stent retaining means such as elastomeric sleeves or socks. The socks are disposed about the ends of the stent and the respective adjacent portions of the catheter shaft. Socks may be constructed such that during balloon inflation the socks release the stent as a result of the forces and change in geometry resulting from the expanding balloon. It is also known that socks may be constructed to retract or be pulled off of the stent as a result of their construction and the expansion of the balloon.

Inflation expandable stent delivery and deployment assemblies are known which utilize restraining means that overlie the stent during delivery. U.S. Pat. No. 4,950,227 to Savin et al., relates to an inflation expandable stent delivery system in which a sleeve overlaps the distal or proximal margin (or both) of the stent during delivery. During inflation of the stent at the deployment site, the stent margins are freed of the protective sleeve(s). U.S. Pat. 5,403,341 to Solar, relates to a stent delivery and deployment assembly which uses retaining sheaths positioned about opposite ends of the compressed stent. The retaining sheaths of Solar are adapted to tear under pressure as the stent is radially expanded, thus releasing the stent from engagement with the sheaths. U.S. Pat. No. 5,108,416 to Ryan et al., describes a stent introducer system which uses one or two flexible end caps and an annular socket surrounding the balloon to position the stent during introduction to the deployment site. The content of all references, including patents and patent applications are respectively incorporated it their entirety herein by reference.

Providing a means for containing and securing the stent or other medical device on the balloon catheter prior to inflation is but one problem facing stent delivery systems. An additional concern is the shifting or sliding of the stent relative to the balloon during balloon expansion. Numerous attempts have been made to reduce or prevent translocation of the stent on the balloon during balloon expansion. For example: copending U.S. patent application Ser. No. 09/667,916, filed Sep. 22, 2000 and entitled Coated Stents with Better Gripping Ability, describes a stent coating which provides the stent with improved ability to adhere to the balloon during the expansion process. Another example is U.S. Pat. No. 5,836,965 which describes a process wherein a balloon is expanded and heat set then allowed to cool in order to adhere the balloon to the stent. Yet another example is co-pending U.S. patent application Ser. No. 08/740,727, filed Nov. 1, 1996, which issued as U.S. Pat. No. 6,306,144 and is entitled Selective Coating Of A Balloon Catheter With Lubricous Material For Stent Deployment, which describes a balloon having a tacky coating for securing a stent to a balloon prior to delivery.

The entire content of all of the patents and patent applications listed within the present patent application are respectively incorporated in their entirety herein by reference.

BRIEF SUMMARY OF THE INVENTION

The present invention addresses the problem of longitudinal stent movement during balloon expansion by providing a stent delivery system with a balloon which when in the unexpanded state has a stent mounting region having a central diameter which is either greater or less than that of the adjacent portions of the stent mounting region of the balloon. Wherein the central portion is wider, the central portion provides an engagement point between the balloon and stent. In the embodiment where the central portion has a lesser diameter, the end portions of the stent mounting region provides a pair of engagement points between the balloon and stent. Unlike many prior art systems, where the balloon cones tend to inflate first, the balloon of the present invention is designed to expand initially at the engagement point of the wider central portion or the wider end portions of the stent mounting region thereby providing continual central engagement between the balloon and stent throughout the expansion process.

BRIEF DESCRIPTION OF THE SEVERAL VIEWS OF THE DRAWINGS

A detailed description of the invention is hereafter described with specific reference being made to the drawings in which.

DETAILED DESCRIPTION OF THE INVENTION

Figure 1:
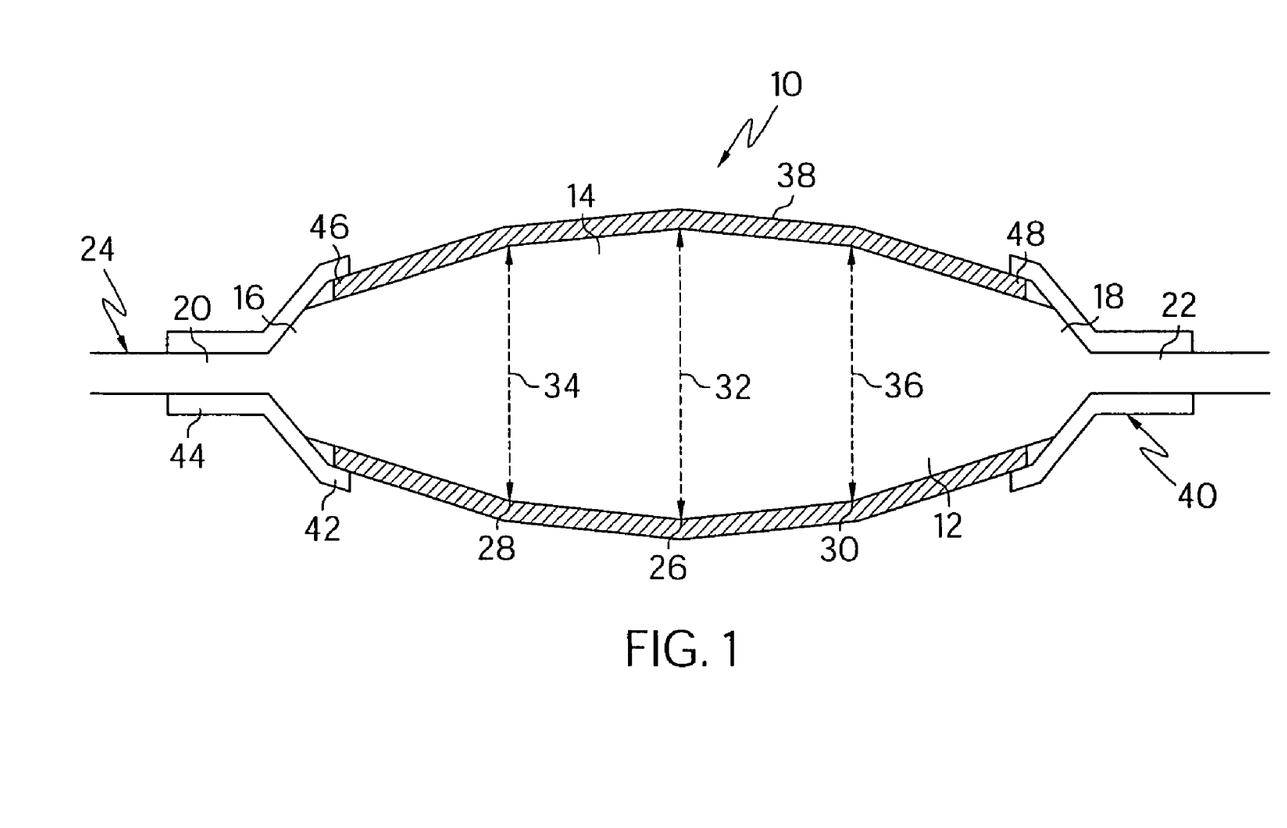
FIG. 1 is a side view of an embodiment of the invention wherein the balloon is in the unexpanded state.
Figure 3:
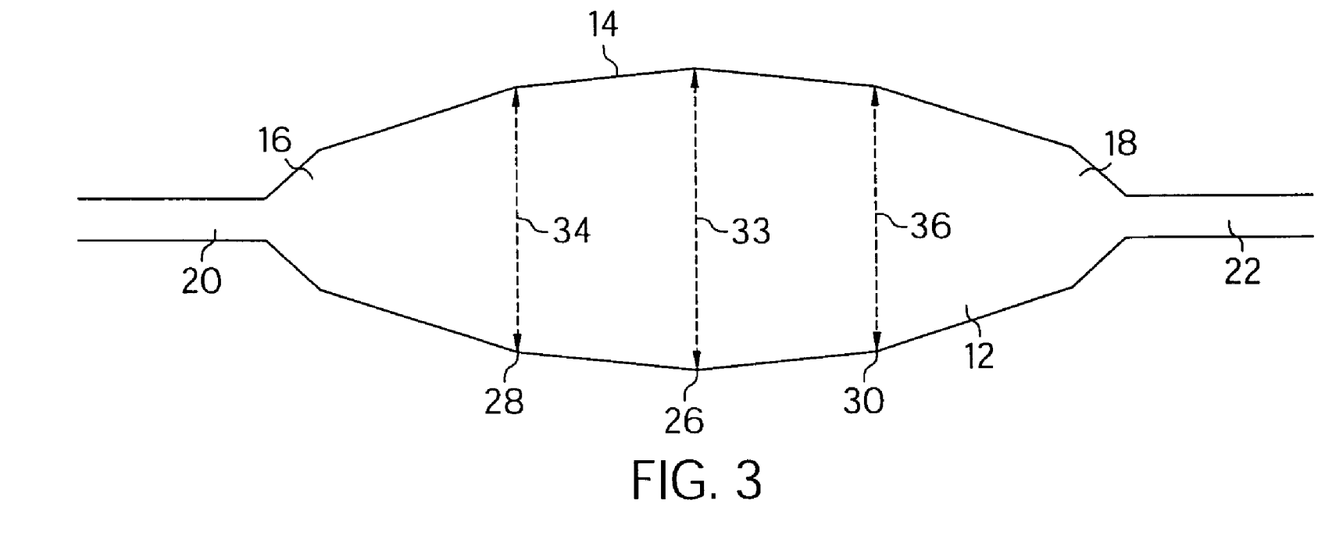
FIG. 3 is a side view of an embodiment of the invention wherein the balloon is shown without a stent delivery catheter.

As may be seen in FIG. 1, the present invention may be directed to a stent delivery catheter, such as is generally indicated at 10. The catheter 10 includes an inflatable portion or balloon 12. The balloon 12, such as may best be seen in FIG. 3, includes a stent delivery region 14 and a pair of balloon cones 16 and 18 adjacent thereto.

Figure 4:
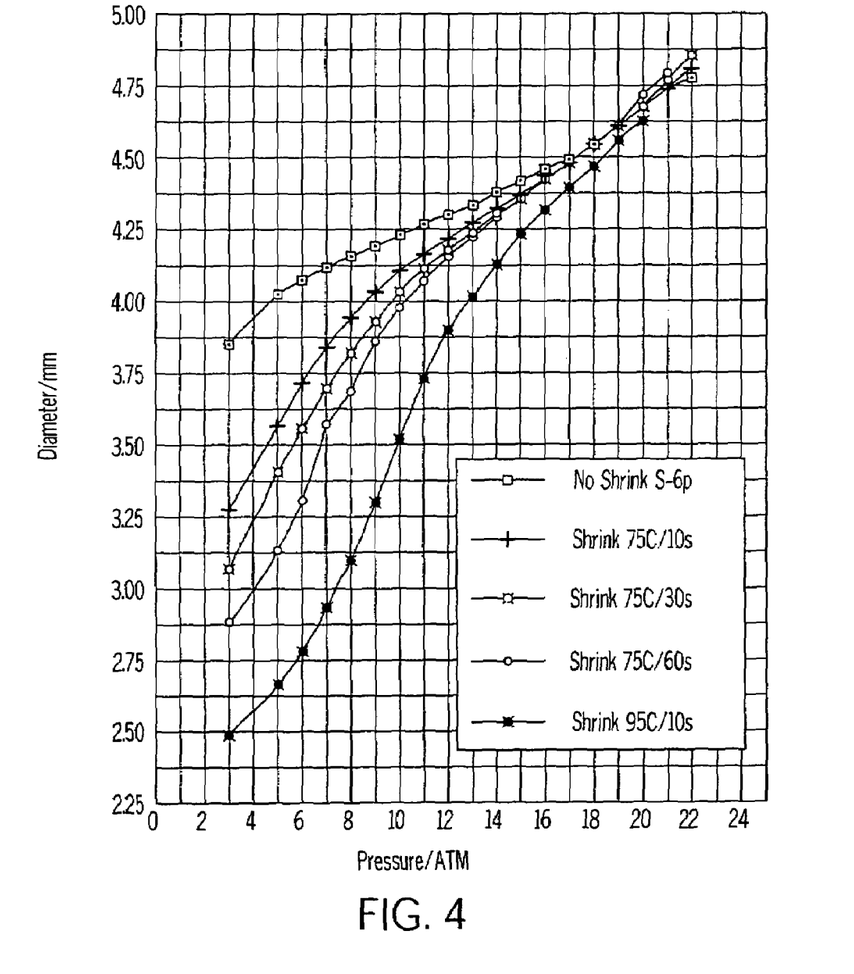
FIG. 4 is a graph illustrating the compliance curve of an embodiment of a balloon.
Figure 5:
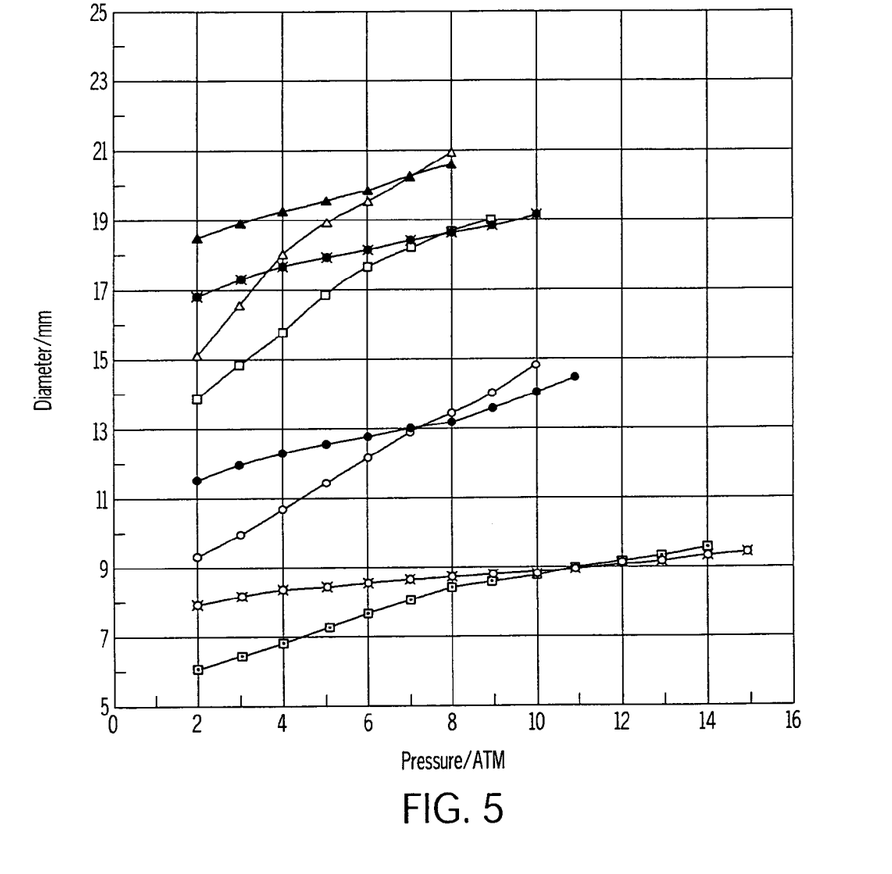
FIG. 5 is a graph illustrating the compliance curve of another embodiment of a balloon.

Balloon 12 maybe composed of any thermoplastic polymer, or polymers, suitable for use as a medical balloon. Such thermoplastic polymers include, but are not limited to; polyesters, polyethylene terephthalate (PET), polybutylene terephthalate (PBT), PEBAX™ (polyether-block polyamide polymer), Nylon™, polyurethane, polyester-polyether block copolymer such as ARNITEL™ (polyester-polyether block copolymer), polyolefin and polyolefin compounds. In addition, the present balloon may be manufactured by any means appropriate for manufacture a medical balloon. One such approach involves fanning a balloon by stretching and blowing of the balloon from a segment of extruded polymer tubing. Methods of forming the balloon of the present invention may include the following:

Providing Pebax® 7233 tubes with dimensions of 0.105 inch ID (inner diameter)×0.140 OD (outer diameter) are cold-drawn at a very low temperature, approximately in the range of −100° C. to −20° C. as follows. A screw driven stretching machine with a pair of pneumatic grippers is used to stretch the tubing. The center portion of the tube is cooled by directly spraying liquid $N_2$ on the center portion. Five 50 mm length balloons are blown at about 5 psi pressure, were shrunk by annealing the balloons in water baths under different conditions, namely: 75° C. for 10 seconds; 75° C. for 30 seconds; 75° C. for 60 seconds; and 95° C. for 10 seconds. Compliance curves for such a balloon may be seen in FIG. 4. Alternatively, the balloons may be prepared as above using Pebax® 7033 polymer, the compliance results are plotted in FIG. 5.

The forming processes described above are described in greater detail in the examples provided in co-pending U.S. Application Ser. No. 08/685,338 filed Jul. 23, 1996 and entitled High Compliance, High Strength Catheter Balloons Useful for Treatment of Gastrointestinal Lesions, the entire contents of which being incorporated herein by reference.

While other potential means of forming the balloon of the present invention may exist such unconventional methods are not typically used. However, such possible methods may include: preparing a balloon by joining multiple segments of tubing having the appropriate dimensions such as shown, end-to-end via the use of heat or adhesive welding. When using such a process it may be possible to provide a balloon where, for instance, the ends are made from a first polymer material, and the body portion made from a second polymer material. Other balloon forming processes may be possible.

The balloon may also be constructed through the well known process of extruding the balloon material into a preform and conventionally blowing the balloon. The balloon material may be extruded uniformly or may be extruded in sequential segments and subsequently bonded together. Other methods may be available which are suitable for the construction of balloon 12.

The end cones 16 and 18 each include a waist portion 20 and 22. Where the balloon 12 is included with a stent delivery system, such as with a catheter 10 shown in FIGS. 1 and 2, the waist portions 20 and 22 may be portions of the catheter shaft 24 or may be engaged thereto. The stent delivery region 14 has a unique configuration which includes a central portion 26 and a pair of end portions 28 and 30.

As is know to those of skill in the art, when a medical balloon of catheter is in the unexpanded state, the balloon will typically include one or more folds. The folded configuration of the balloon provides numerous benefits to the catheter device. An example of a folded balloon is described in U.S. patent application Ser. No. 09/335,361, filed Jun. 17, 1999, which issued as U.S. Pat. No. 6,280,412 and is entitled Stent Securement By Balloon Modification, the entire contents of which being incorporated herein by reference. The balloon 12 depicted in FIG. 1 is shown in a partially inflated state wherein the balloon 12 has unfolded by an internal inflation pressure of about 1 to about 2 atmospheres. Despite, being "unfolded", the balloon 12 as shown in FIG. 1 is referred to herein as being in an unexpanded or non-inflated state. In the non-inflated state, the central portion 26 has a diameter 32 which is greater than the diameters 34 and 36 of the respective end portions 28 and 30. The central portion 26 will have a diameter 32 which is between about 0.1 to 0.25 mm greater than the diameters 34 and 36 of the respective end portions 28 and 30.

As has been indicated above, a catheter 10 may be employed for the delivery of a medical device, such as a stent 38. Stent 38 is loaded on to the stent delivery region 14 prior to insertion into a body lumen or vessel.

In many prior stent delivery systems, the balloon is configured to initially expand at or near the balloon cones, with the central region of the balloon inflating thereafter. This delay in inflation of the central region of the balloon may potentially result in the ends or an end of the balloon expanding first which in turn could potentially result in dislocation or sliding of the stent relative to the balloon surface. Such sliding is often described as a "water melon seed effect," and may have detrimental results.

To prevent the "water melon seed effect" as well as other less dramatic forms of dislocation of the stent, in the present invention the greater diameter 32 of the central portion 26 of the stent delivery region 14 provides the balloon 12 with the ability to expand initially at the center portion 26, which in turn provides a continual engagement surface between the stent 38 and balloon 12 during expansion. By providing a continual engagement between the center portion 26 of the balloon 12 and the stent 38, the present invention prevents movement of the stent 38 relative to the balloon 12 during balloon inflation and stent 38 expansion.

As indicated above a variety of devices, such as sheathes and/or sleeves or socks, may be used to retain a stent on a stent delivery balloon. In the present invention such as may be seen in FIG. 1, the catheter 10 is equipped with at least one retractable stent retaining sleeve 40, which retains the stent 38 in the unexpanded state prior to balloon inflation. In the embodiment shown, the catheter 10 has a pair of stent retaining sleeves 40. Each sleeve 40 has a stent retaining portion 42 and a catheter engagement portion 44. When the balloon 12 is in the unexpanded state such as is shown in FIG. 1, the stent retaining portion 42 is disposed about the proximal end 46 and distal end 48 respectively of the stent 38. The catheter engagement portion 44 is disposed about the respective waist portions 20 and 22 of the catheter shaft 24. The catheter engagement portion of the sleeve 40 may be frictionally engaged to the catheter shaft 24 or may be engaged in any suitable manner such as by, laser welding, chemical welding, adhesive bonding, etc.

Figure 2:
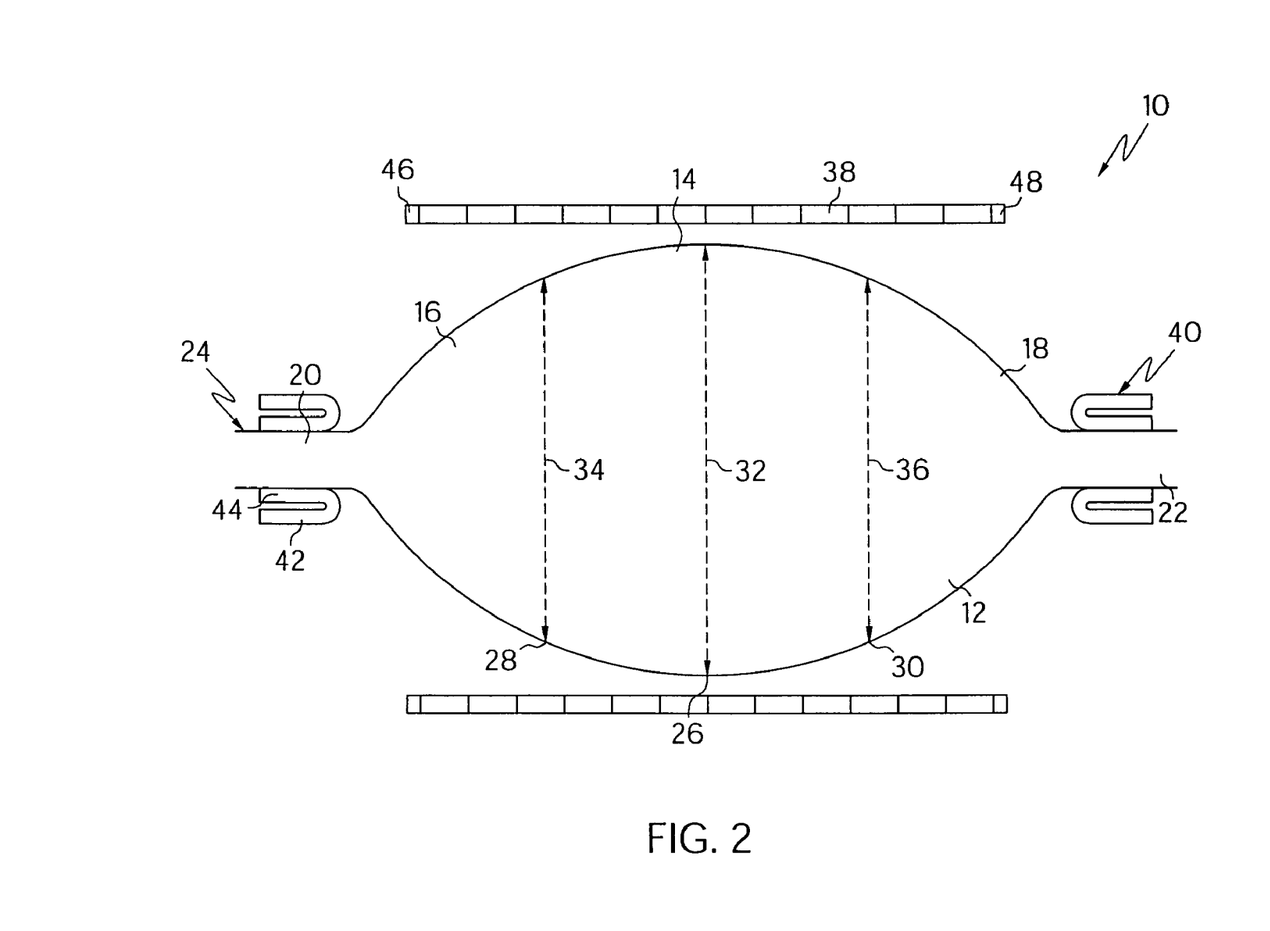
FIG. 2 is a side view of the embodiment of the invention shown in FIG. 1 wherein the balloon is in the expanded state.

When the balloon 12 is inflated such as is shown in FIG. 2, the stent 38 expands to the expanded state. As the stent 38 expands, the sleeves 40 are retracted off of the stent ends 46 and 48. Stent retaining sleeves 40 maybe configured to have a variety of retraction characteristics or modes. For example, the sleeves 40 may be configured to merely pull back off of the end 46 and 48 of the stent 38. Alternatively, the sleeves 40 or a portion thereof, such as the stent retaining portion 42, may be configured to fully retract off of the stent 38 as well as the cones 16 and 18 such as is shown. Where the sleeves 40 are constructed to retract off of the stent 38, they may be retracted by providing the sleeves 40 with a retraction mode such as the "S-mode" shown in FIG. 2. Other types of retraction characteristics are also described in co-pending U.S. patent application Ser. No. 09/407,836, filed Sep. 28, 1999, which issued as U.S. Pat. No. 6,478,814 and is entitled Stern Securement Sleeves and Optional Coatings and Methods of Use, the entire content of which being incorporated herein by reference.

It should be noted that the interface between the central portion 26 of the balloon 12 and the stent 38 helps to prevent stent longitudinal stent dislocation relative to the balloon 12 even after the stent 38 is expanded beyond the sleeves 40 and/or subsequent to sleeve retraction up until the point when the balloon 12 is fully expanded and the stent 38 is delivered, such as is shown in FIG. 2. When the balloon 12 is fully expanded the various diameters 32, 34 and 36 are substantially the same.

Figure 6:
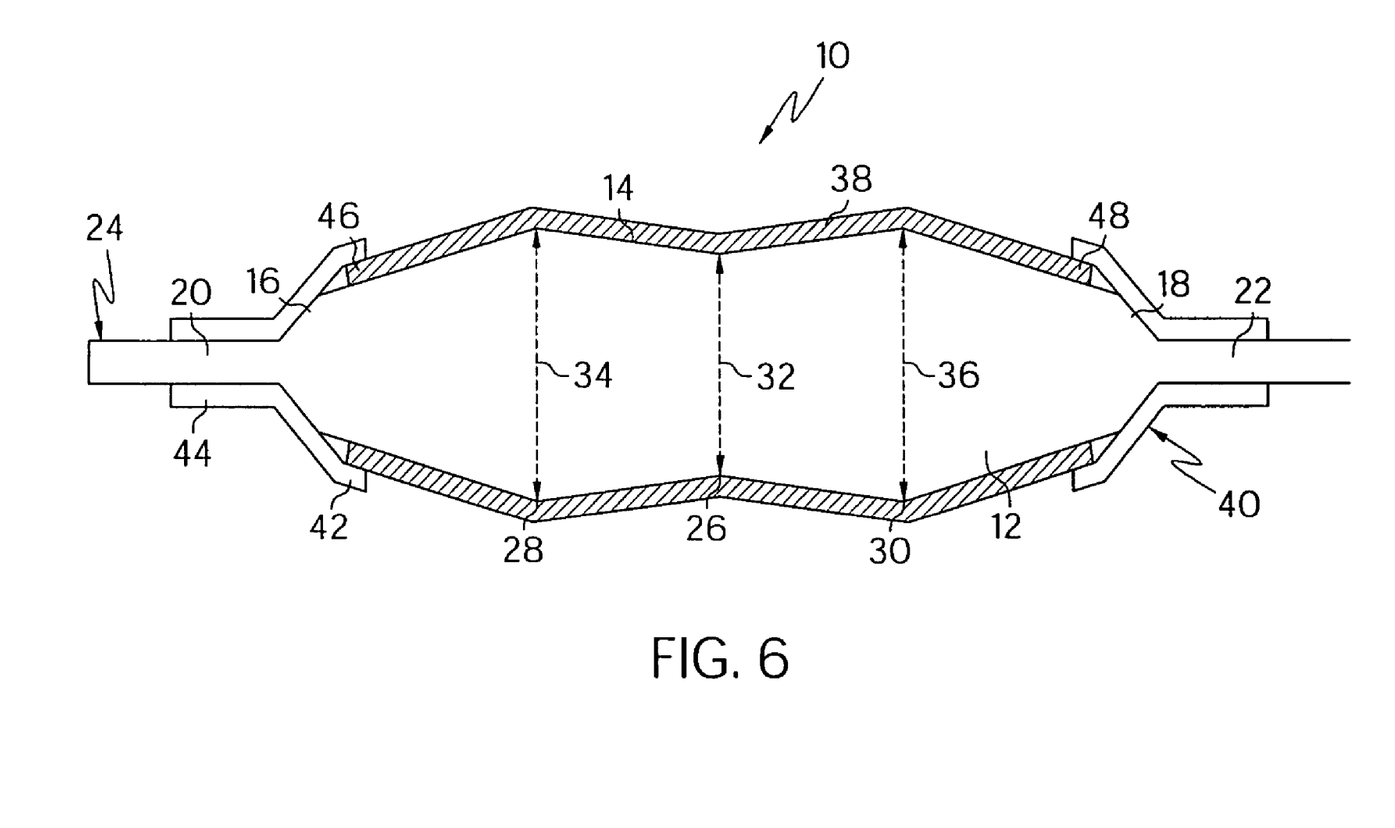
FIG. 6 is a side view of an alternative embodiment of the invention.

In an alternative embodiment of the invention shown in FIG. 6 the catheter 10 may include balloon 12 which has a stent mounting region 14 having a central portion 26 which when in the non-inflated state has a diameter 32 less than the diameters 34 and 36 of the end portions 28 and 30. In the embodiment shown the central portion 26 will have a diameter 32 which is between about 0.1 to 0.25 mm less than the diameters 34 and 36 of the respective end portions 28 and 30. By providing the balloon 12 with a central portion 26 which has a smaller diameter 32 than the respective diameters 34 and 36 of the end portions 28 and 30, the end portions 28 and 30 effectively provide a pair of engagement surfaces between the balloon 12 and the stent 38 during balloon inflation. In the inflated state, the diameter of the central portion 26 is substantially the same as the diameters 34 and 36, such as is depicted in FIG. 2.

Figure 7:
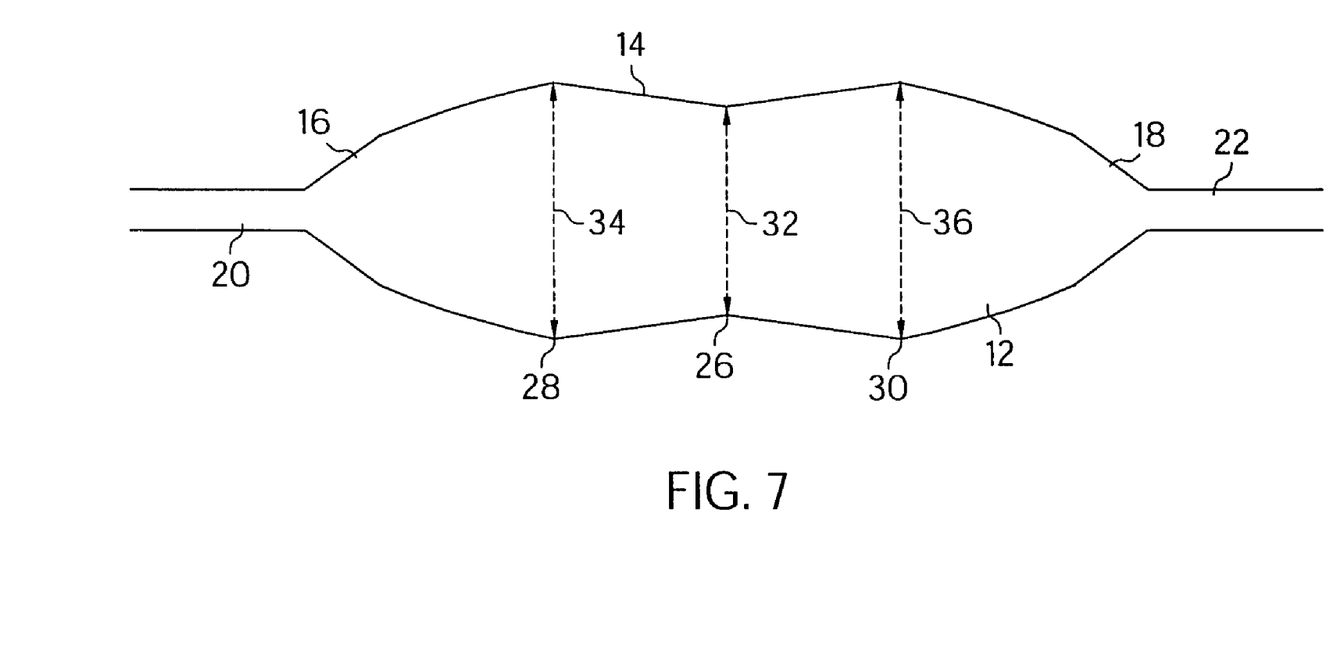
FIG. 7 is a side view of an embodiment of the invention wherein the balloon is shown without a stent delivery catheter.

In FIG. 6, the balloon 12 is depicted in use with a catheter 10. However, the unique features of the balloon 12 may best be seen in FIG. 7 wherein the balloon is depicted alone.

Configurations, other than those described above and depicted in the various Figures of the balloon may be possible, so as to provide the balloon and stent with a variety of engagement surfaces.

In addition to being directed to the embodiments described above and claimed below, the present invention is further directed to embodiments having different combinations of the features described above and claimed below. As such, the invention is also directed to other embodiments having any other possible combination of the dependent features claimed below.

The above examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

The invention claimed is:

1. A stent delivery system comprising:
   a catheter, the catheter having a catheter shaft;
   a medical balloon mounted on the catheter shaft, the medical balloon having a non-inflated state and being inflatable to an inflated state, the medical balloon having a stent mounting region, and a stent disposed about at least a portion of the stent mounting region, the start having an unexpanded state and an expanded state, the stent further having a stent center, a first stent end, and a second stent end,
   the stent mounting region having a middle portion, a first end portion adjacent to the middle portion and a second end portion adjacent to the middle portion, the middle portion having a middle portion diameter, the first end portion having a first end portion diameter, the second end portion having a second end portion diameter,
   in the non-inflated state the middle portion diameter being greater than the first end portion diameter and the second end portion diameter,
   in the inflated state the balloon providing the middle portion diameter with a diameter substantially the same as that of the first end portion diameter and the second end portion diameter; wherein when the medical balloon is expanded, the middle portion pushes against the stent before the first end portion and before the second end portion, and wherein when the balloon is expanded from the non-inflated state to the inflated state the stent is expanded from the unexpanded state to the expanded state, such that the stent center is expanded before the first stent end and before the second stent end.

2. The stent delivery system of claim 1 wherein when the balloon is in the non-inflated state the middle portion diameter is between about 0.1–0.25 mm greater than the first end portion diameter and the second end portion diameter.

3. The stent delivery system of claim 1, the medical balloon further comprising:

a first cone, the first cone being immediately adjacent to the first end portion, the first cone having a first waist, the first waist having a first waist diameter, the first waist engaged to a first portion of the catheter shaft, the first end portion diameter being greater than the first waist diameter; and a second cone, the second cone being immediately adjacent to the second end portion, the second cone having a second waist, the second waist having a second waist diameter, the second waist engaged to a second portion of the catheter shaft, the second end portion diameter being greater than the second waist diameter.

4. The stent delivery system of claim 1 further comprising at least one stent retaining sleeve, the at least one stent retaining sleeve having a stent retaining portion disposed about one end of the stent and a catheter engagement portion engaged to a portion of the catheter shaft adjacent to the medical balloon.

5. The stent delivery system of claim 1 wherein the at least one stent retaining sleeve being refracted off of the stent end during expansion of the stent, thereby releasing the stent from the at least one stent retaining sleeve.

6. The stent delivery system of claim 1 wherein the balloon is manufactured from at least one member of the group consisting of: polyesters, polyethylene terephthalate, polybutylene terephthalate, polyether-block polyamide polymer, Nylon, polyurethane, polyester-polyether block copolymer, polyolefin, polyolefin compounds and any combinations thereof.

7. A stent delivery system comprising:

a catheter, the catheter having a catheter shaft;

a medical balloon mounted on the catheter shaft, the medical balloon having a non-inflated state and being inflatable to an inflated state, the medical balloon having a stent mounting region, and a stent disposed about at least a portion of the stent mounting region, the stent mounting region having a middle portion, a first end portion adjacent to the middle portion and a second end portion adjacent to the middle portion, the middle portion having a middle portion diameter, the first end portion having a first end portion diameter, the second end portion having a second end portion diameter, in the non-inflated state the middle portion diameter being less than the first end portion diameter and the second end portion diameter, in the inflated state the middle portion diameter being substantially the same as the first end portion diameter and the second end portion diameter.

8. The stent delivery system of claim 7 whereby, when the medical balloon is expanded the first end portion and to second end portion pushes against the stent before the middle portion.

9. The stent delivery system of claim 7 wherein when the balloon is in the non-inflated state the middle portion diameter is between about 0.1–0.25 mm less than the first end portion diameter and the second end portion diameter.

10. The stent delivery system of claim 7, the medical balloon further comprising:

a first cone, the first cone being immediately adjacent to the first end portion, the first cone having a first waist, the first waist having a first waist diameter, the first waist engaged to a first portion of the catheter shaft, the first end portion diameter being greater than the first waist diameter; and a second cone, the second cone being immediately adjacent to the second end portion, the second cone having a second waist, the second waist having a second waist diameter, the second waist engaged to a second portion of the catheter shaft, the second end portion diameter being greater than the second waist diameter.

11. The stent delivery system of claim 7 further comprising at least one stent retaining sleeve, the at least one stent retaining sleeve having a stent retaining portion disposed about one end of the stent and a catheter engagement portion engaged to a portion of the catheter shaft adjacent to the medical balloon.

12. The stent delivery system of claim 7, the stent comprising an unexpanded state and an expanded state, the stent further comprising a stent center, a first stent end and a second stent end.

13. The stent delivery system of claim 12 further comprising at least one stent delivery sleeve, the at least one stent retaining sleeve being retracted off of the stent ends during expansion of the stent, thereby releasing the stent from the at least one stent retaining sleeve.

14. The stent delivery system of claim 7 wherein the balloon is manufactured from at least one member of the group consisting of: polyesters, polyethylene terephthalate, polybutylene terephthalate, polyether-block polyamide polymer, Nylon, polyurethane, polyester-polyether block copolymer, polyolefin, polyolefin compounds and any combinations thereof.

15. A stent delivery balloon having a non-inflated state and being inflatable to an inflated state, the balloon comprising:

a stent mounting region, at least a portion of the stent mounting region being constructed and arranged to disposingly receive a stent thereabout, the stent mounting region having a middle portion, a first end portion adjacent to the middle portion and a second end portion adjacent to the middle portion, the middle portion having a middle portion diameter, the first end portion having a first end portion diameter, the second end portion having a second end portion diameter, in the non-inflated state the middle portion diameter being less than the first end portion diameter and the second end portion diameter, in the inflated state the middle portion diameter being substantially the same as the first end portion diameter and the second end portion diameter;

a first cone, the first cone being immediately adjacent to the first end portion, the first cone having a first waist, the first waist having a first waist diameter, the first end portion diameter being greater than the first waist diameter; and a second cone, the second cone being immediately adjacent to the second end portion, the second cone having a second waist, the second waist having a second waist diameter, the second end portion diameter being greater than the second waist diameter.

16. A stent delivery balloon having a non-inflated state and being inflatable to an inflated state, the neat delivery balloon comprising:
a stent mounting region, the stent mounting region having a middle portion, a first end portion adjacent to the middle portion and a second end portion adjacent to the middle portion, the middle portion having a middle portion diameter, the first end portion having a first end portion diameter, the second end portion having a second end portion diameter, in the non-inflated state the middle portion diameter being less than the first end portion diameter and the second end portion diameter, in the inflated state the middle portion diameter being substantially the same as the first end portion diameter and the second end portion diameter.

* * * * *

UNITED STATES PATENT AND TRADEMARK OFFICE
CERTIFICATE OF CORRECTION

PATENT NO. : 7,037,318 B2 Page 1 of 1
APPLICATION NO. : 09/740101
DATED : May 2, 2006
INVENTOR(S) : Lixiao Wang It is certified that error appears in the above-identified patent and that said Letters Patent is hereby corrected as shown below:

Column 6, Line 52, delete "start" and insert --stent--.

Signed and Sealed this

Tenth Day of February, 2009

JOHN DOLL
*Acting Director of the United States Patent and Trademark Office*